United States Patent
Oh et al.

(10) Patent No.: US 11,635,549 B2
(45) Date of Patent: Apr. 25, 2023

(54) REFLECTIONLESS WINDOW, METHOD FOR MANUFACTURING SAME, AND REFLECTIONLESS WINDOW FOR INVASIVE SENSOR

(71) Applicant: SAMSUNG ELECTRONICS CO., LTD., Suwon-si (KR)

(72) Inventors: Young-jae Oh, Suwon-si (KR); Chul-ho Cho, Yongin-si (KR); Kwang-bok Kim, Incheon (KR); Seong-je Cho, Suwon-si (KR); Youn-joo Song, Yongin-si (KR); Hyoung-seon Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 907 days.

(21) Appl. No.: 16/470,341

(22) PCT Filed: Dec. 21, 2017

(86) PCT No.: PCT/KR2017/015287
§ 371 (c)(1),
(2) Date: Jun. 17, 2019

(87) PCT Pub. No.: WO2018/117710
PCT Pub. Date: Jun. 28, 2018

(65) Prior Publication Data
US 2020/0116898 A1 Apr. 16, 2020

(30) Foreign Application Priority Data

Dec. 21, 2016 (KR) .................. 10-2016-0175746

(51) Int. Cl.
*G02B 1/118* (2015.01)
*B82Y 20/00* (2011.01)
*A61B 5/00* (2006.01)

(52) U.S. Cl.
CPC ............ *G02B 1/118* (2013.01); *A61B 5/0086* (2013.01); *B82Y 20/00* (2013.01)

(58) Field of Classification Search
CPC ............ G02B 1/118; G02B 1/11; B82Y 20/00
See application file for complete search history.

(56) References Cited

U.S. PATENT DOCUMENTS

| 8,160,665 B2 | 4/2012 | Mischler et al. |
| 9,653,625 B2 | 5/2017 | Myoung et al. |
| (Continued) | | |

FOREIGN PATENT DOCUMENTS

| JP | 2007-216030 A | 8/2007 |
| JP | 2008-99991 A | 5/2008 |
| JP | 2011-519635 A | 7/2011 |
| (Continued) | | |

OTHER PUBLICATIONS

International Search Report dated Mar. 30, 2018 by the International Searching Authority in counterpart International Patent Application No. PCT/KR2017/015287. (PCT/ISA/210).
(Continued)

*Primary Examiner* — Cara E Rakowski
(74) *Attorney, Agent, or Firm* — Sughrue Mion, PLLC

(57) ABSTRACT

A reflectionless window is disclosed. The reflectionless window comprises: a transparent window; a plurality of first nanocolumns arranged on a first surface of the transparent window; and a plurality of second nanocolumns having a height smaller than that of the first nanocolumns, the plurality of second nanocolumns being arranged on at least one surface selected from the upper surface of the plurality of first nanocolumns and a side surface thereof and being arranged in an area on the first surface of the transparent window in which the plurality of first nanocolumns are not arranged.

11 Claims, 19 Drawing Sheets

(56) References Cited

U.S. PATENT DOCUMENTS

| | | | | |
|---|---|---|---|---|
| 2004/0125266 A1* | 7/2004 | Miyauchi | ............... | G02B 1/118 349/57 |
| 2006/0052709 A1* | 3/2006 | DeBaryshe | .......... | A61B 5/0075 600/476 |
| 2009/0099537 A1 | 4/2009 | DeVoe et al. | | |
| 2009/0131905 A1 | 5/2009 | Allen et al. | | |
| 2010/0121163 A1* | 5/2010 | Vestel | ............... | A61B 5/14532 600/316 |
| 2011/0276003 A1* | 11/2011 | Luttge | ............... | A61M 37/0015 264/293 |
| 2012/0026591 A1* | 2/2012 | Hayashibe | ........ | G02F 1/133502 359/601 |
| 2013/0155522 A1 | 6/2013 | Jeong et al. | | |
| 2013/0298977 A1* | 11/2013 | Chen | ...................... | B82Y 30/00 257/618 |
| 2014/0211206 A1 | 7/2014 | Wang et al. | | |
| 2016/0331238 A1* | 11/2016 | Kim | ..................... | A61B 5/0075 |
| 2016/0370505 A1* | 12/2016 | Koo | .................. | H01L 27/14625 |
| 2018/0100957 A1* | 4/2018 | Ye | ........................ | G02B 5/0294 |

FOREIGN PATENT DOCUMENTS

| | | |
|---|---|---|
| KR | 10-2009-0072462 A | 7/2009 |
| KR | 10-1113691 B1 | 2/2012 |
| KR | 10-2012-0094550 A | 8/2012 |
| KR | 10-2013-0014135 A | 2/2013 |
| KR | 10-1300188 B1 | 8/2013 |
| KR | 10-2016-0132741 A | 11/2016 |
| WO | 2009/135197 A2 | 11/2009 |
| WO | WO-2016026983 A1 * 2/2016 ............... G02B 1/02 |  |

OTHER PUBLICATIONS

Written Opinion dated Mar. 30, 2018 by the International Searching Authority in counterpart International Patent Application No. PCT/KR2017/015287. (PCT/ISA/237).

\* cited by examiner

GENERAL PLANE (a)

REFLECTIONLESS STRUCTURE (b)

1

REFLECTIONLESS WINDOW, METHOD FOR MANUFACTURING SAME, AND REFLECTIONLESS WINDOW FOR INVASIVE SENSOR

TECHNICAL FIELD

This disclosure relates to a reflectionless window, a manufacturing method thereof, and a reflectionless window for an invasive sensor and, more specifically, to a reflectionless window including a plurality of nanocolumns, a manufacturing method thereof, and a reflectionless window for an invasive sensor.

BACKGROUND ART

Generally, to reduce an amount of reflection of light between two media having different refractive indexes is a very important problem to be solved for an optical element such as a display and a sensor.

The reflection of light is a major cause to deteriorate efficiency of the optical element, and as much as the reflection of light is minimized, a higher efficiency may be obtained.

In order to reduce a loss caused by the reflection of light, a film having an intermediate refractive index between the refractive indices of the two media, and the like, has been used. However, the reflectionless film has a problem in that, as the reflective index of the film is decided at the time of manufacturing and thus, when any one medium is changed or the wavelength of transmitted light is changed, the reflectionless effect is deteriorated.

Accordingly, there is a need for a reflectionless structure applicable in various environments.

DETAILED DESCRIPTION

Technical Problem

The disclosure is to solve the above problems and is purposed to provide a reflectionless window, a method for manufacturing the same, and a reflectionless window for an invasive sensor and, more particularly, to a reflectionless window including a plurality of nanocolumns, a method for manufacturing the same, and a reflectionless window for an invasive sensor.

Technical Solution

According to an embodiment of the disclosure, a reflectionless window includes a transparent window, a plurality of first nanocolumns arranged on a first surface of the transparent window, and a plurality of second nanocolumns having a height smaller than a height of the first nanocolumns, the plurality of second nanocolumns being arranged on at least one surface from an upper surface and a side surface of the plurality of first nanocolumns and being arranged in an area on a surface of the transparent window in which the plurality of first nanocolumns are not arranged.

The plurality of first nanocolumns and the plurality of second nanocolumns are made of a same material as the transparent window.

The first nanocolumn may have a height of 130 nm to 390 nm and a width of 70 nm to 210 nm, and the second nanocolumn may have a height less than or equal to 65 nm and a width less than or equal to 35 nm.

The transparent window may be formed with any one material among glass, acryl, Polyethylene Terephthalate (PET), Polyethylene Naphthalate (PEN), Polymethylmethacrylate (PMMA), Colorless Polyimide (CIP), polyethylene, polypropylene, polysulfone, polyurethane, polyether ether ketone, polythermide, polycarbonate, polyaniline, cyclic olefin copolymer, and silk.

The plurality of first nanocolumns may be configured such that a size of an upper surface which is smaller than a size of a lower surface that is in contact with a surface of the transparent window.

A method for manufacturing a reflectionless window according to an embodiment includes forming a plurality of first nanocolumns by etching an upper portion of a transparent window and by secondarily etching the upper portion of the transparent window in which the plurality of first nanocolumns are formed, forming a plurality of second nanocolumns arranged on at least one surface among the upper surface of the plurality of first nanocolumns and side surface thereof, and in an area on a surface of the transparent window, in which the plurality of first nanocolumns are not arranged, respectively.

The forming the plurality of first nanocolumns may include arranging the first nanoislands in an upper area of the transparent window corresponding to the plurality of first nanocolumns and etching an upper portion of the transparent window in which the first nanoislands are arranged.

In this case, the forming the plurality of first nanocolumns may further include the removing the first nanoislands after the etching.

In the meantime, the etching may include removing the first nanoislands at the same time with etching an area where the first nanoislands are not arranged.

The forming the plurality of second nanocolumns may include arranging second nanoislands which are smaller than the first nanoislands on an area corresponding to the plurality of second nanocolumns, from among at least one of an upper surface and a side surface of the plurality of first nanocolumns, and an upper area of the transparent window where the plurality of first nanocolumns are not arranged, and secondarily etching the upper part of the transparent window in which the second nanoislands are arranged.

The forming the plurality of second nanocolumns may further include the removing the second nanoislands after the secondary etching.

The secondary etching may include removing the second nanoislands at the same time with etching the area where the second nanoislands are not arranged.

The at least one of the first nanoislands and the second nanoislands may be formed with at least one of polystyrene and glass.

At least one of the first nanoislands and the second nanoislands may be formed with at least one of gold, silver, aluminum, chrome, copper, and titanium.

The diameter of the first nanoislands may be between 70 nm and 210 nm and the diameter of the second nanoislands may be 35 nm or less.

According to an embodiment, a reflectionless window for an invasive sensor includes a transparent window, a microstructure which is arranged on an upper part of the transparent window and has a shape of a needle to penetrate a skin layer, and a plurality of nanocolumns arranged on an end of the microstructure.

The reflectionless window for an invasive sensor may further include a plurality of nanocolumns arranged on a lower part of the transparent window.

The reflectionless window for an invasive sensor may further include a plurality of nanocolumns on a side surface of the microstructure.

The plurality of nanocolumns may include a plurality of first nanocolumns arranged on an end of the microstructure, and a plurality of second nanocolumns having a height smaller than a height of the first nanocolumns, the plurality of second nanocolumns being arranged in an upper surface of the first nanocolumn and an area where the first nanocolumns are not arranged among ends of the microstructure.

The first nanocolumn may have a height of 130 nm to 390 nm and a width of 70 nm to 210 nm, and the second nanocolumn may have a height less than or equal to 65 nm and a width less than or equal to 35 nm.

According to an embodiment, a reflectionless window for a sensor includes a transparent window in a shape of an optical fiber, and a plurality of first nanocolumns arranged on a surface of the transparent window.

The reflectionless window for a sensor may further include a plurality of first nanocolumns arranged on another surface which is opposite to the surface of the transparent window.

The transparent window may include a microstructure in a shape of a needle arranged on an upper part of the transparent window, and the plurality of first nanocolumns may be arranged on at least one of an end or a side surface of the microstructure.

The plurality of first nanocolumns may include a plurality of second nanocolumns having a height smaller than a height of the first nanocolumns, the plurality of second nanocolumns being arranged on at least one surface from an upper surface and a side surface of the plurality of first nanocolumns and being arranged in an area on a surface of the transparent window, in which the plurality of first nanocolumns are not arranged.

The first nanocolumn may have a height of 130 nm to 390 nm and a width of 70 nm to 210 nm, and the second nanocolumn may have a height less than or equal to 65 nm and a width less than or equal to 35 nm.

DETAILED DESCRIPTION OF EXEMPLARY EMBODIMENTS

Figure 1:
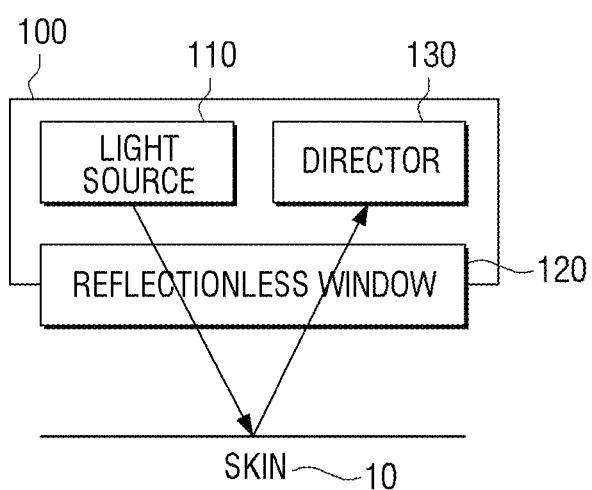
FIG. 1 is a view briefly illustrating a configuration of a sensor including a reflectionless window according to an embodiment.

After terms used in the present specification are briefly described, the present disclosure will be described in detail.

General terms that are currently widely used were selected as terms used in exemplary embodiments of the present disclosure in consideration of functions in the present disclosure, but may be changed depending on the intention of those skilled in the art or a judicial precedent, the emergence of a new technique, and the like. In addition, in a specific case, terms arbitrarily chosen by an applicant may exist. In this case, the meaning of such terms will be mentioned in detail in a corresponding description portion of the present disclosure. Therefore, the terms used in exemplary embodiments of the present disclosure should be defined on the basis of the meaning of the terms and the contents throughout the present disclosure rather than simple names of the terms.

Since the present disclosure may be variously modified and have several exemplary embodiments, specific exemplary embodiments of the present disclosure will be illustrated in the drawings and be described in detail in the detailed description. However, it is to be understood that the present disclosure is not limited to specific exemplary embodiments, but includes all modifications, equivalents, and substitutions without departing from the scope and spirit of the present disclosure. When it is decided that a detailed description for the known art related to the present disclosure may obscure the gist of the present disclosure, the detailed description will be omitted.

Terms 'first', 'second', and the like, may be used to describe various components, but the components are not to be construed as being limited by the terms. The terms are used only to distinguish one component from another component.

Singular forms are intended to include plural forms unless the context clearly indicates otherwise. It will be further understood that terms "include" or "formed of" used in the present specification specify the presence of features, numerals, steps, operations, components, parts, or combinations thereof mentioned in the present specification, but do not preclude the presence or addition of one or more other features, numerals, steps, operations, components, parts, or combinations thereof.

Hereinafter, exemplary embodiments of the present disclosure will be described in detail with reference to the accompanying drawings so that those skilled in the art to which the present disclosure pertains may easily practice the present disclosure. However, the present disclosure may be implemented in various different forms and is not limited to exemplary embodiments described herein. In addition, in the drawings, portions unrelated to the description will be omitted to obviously describe the present disclosure, and similar portions will be denoted by similar reference numerals throughout the specification.

Hereinafter, the present disclosure will be described in detail with reference to the drawings.

FIG. 1 is a view briefly illustrating a configuration of a sensor including a reflectionless window according to an embodiment.

Referring to FIG. 1, a sensor 100 includes a light source 110, a reflectionless window 120, and a detector 130. Specifically, the sensor 100 may measure a biological signal using light. The sensor 100 may measure at least one of a blood glucose, a lactic acid, blood pressure, cholesterol, photoplethysmogram (PPG), electrocardiogram (ECG), a pulse, a respiratory, an oxygen saturation ($S_PO_2$), and a body temperature, by illuminating the surface of skin 10 or hypoderma with light. In addition, the sensor 100 is capable of sensing cancer cells, skin diseases, or the like through measurement of cells. The sensor 100 may irradiate a specific light source or inject a drug for the treatment of a specific part of a human body. The sensor 100 may be used in optogenetics technology to control cells and measure responses of cells by using light.

Herein, the sensor 100 may be various types of sensors, such as a plate type, an invasive type, an optical fiber type, or the like.

Hereinabove, it has been described that a sensor used by the reflectionless window 120 according to various embodiments is a sensor for measuring a biological signal, but the reflectionless window 120 may be applied to all sensors using a light source, such as a proximity sensor and a dimming sensor, as well as a body.

It has been described for convenience of description that the reflectionless window 120 according to various embodiments is used only for a sensor, but in actual implementation, the reflectionless window 120 may be used for all the devices which transmit light such as a TV, a smart phone, a monitor, a tablet PC, or the like, which are operated by transmitting light.

The light source 110 is a configuration which irradiates light. Specifically, the light source 110 may irradiate light onto the surface of the skin 10 or the hypoderma. For example, the light source 110 may use rays of all the wavelength range such as ultraviolet rays, visible rays, infrared rays, near infrared (NIR) rays, or the like. At this time, a plurality of light sources 110 may be formed as needed.

In the meantime, the light source 110 may irradiate light for measurement of a biological signal or a cell. However, the embodiment is not limited thereto, and light for the treatment of the surface of the skin 10 or the hypoderma may be irradiated.

The reflectionless window 120 is a part of the sensor 100 which is in direct contact with the outside, and may transmit light irradiated from the light source 110 or the light reflected from the skin 10 without reflection. Specifically, the reflectionless window 120 may be formed of any of a polymer material which is transparent and is capable of passing light, such as glass, acrylic, polyethylene terephthalate (PET), polyethylene naphthalate (PEN), polymethylmethacrylate (PMMA), colorless polyimide (CPI), polyethylene, polypropylene, polysulfone, polyurethane, polyether ether ketone, polythermide, polycarbonate, polyaniline, cyclic olefin copolymer, silk, or the like. Here, "transparent" may mean that a considerable amount of light passes through, even if the transmittance does not reach 90 to 100%. At this time, the reflectionless window 120 may be in the form of a rigid panel type, a flexible film type, or an optical fiber type composed of flexible fibers. Specifically, when the sensor 100 is in the form of the optical fiber, the reflectionless window 120 in the form of a panel or a flexible film may be attached to the end of the optical fiber opposite to the light source 110 and the detector 130, or the reflectionless window 120 itself may be implemented in the form of the optical fiber.

In the meantime, the reflectionless window 120 may include a transparent window and a plurality of nanocolumns on a surface in direct contact with the outside or a surface in contact with the light source. The specific structure of the reflectionless window 120 will be described later in detail with reference to FIG. 2.

The reflectionless window 120 may further include a microstructure for penetrating the skin. Here, the microstructure may be in the form of a needle for penetrating the skin. Specifically, the reflectionless window 120 may include a microstructure and a plurality of nanocolumns for transmitting light without reflection. The microstructure may be formed of a material such as a transparent window or other materials, and the material forming a microstructure may be a polymer series material which is transparent and is capable of passing light, such as glass, PET, PEN, PMMA, CPI, polyethylene, polypropylene, polysulfone, polyurethane, polyether ether ketone, polythermide, polycarbonate, polyaniline, cyclic olefin copolymer, silk, or the like.

In the meantime, the reflectionless window 120 including the microstructure and the plurality of nanocolumns may be coated with a biodegradable polymer. Here, the biodegradable polymer may be polylactive-co-glycolide (PLGA), polylactic acid (PLA), polyglycolic acid (PGA), poly L-lactic acid (PLLA), polycaproltone (PCL), or the like. As a result, the intensity of the reflectionless window 120 may be improved, and the deformation of the reflectionless window 120 may be minimized even in the process of penetrating the skin.

In the meantime, the biodegradable polymer coating the reflectionless window 120 including the microstructure and a plurality of nanocolumns may include a drug required for a patient, and the biodegradable polymer may be invaded into the skin and then decomposed without deformation, so as to provide the drug to a patient. Various embodiments of the reflectionless window 120 including the above-described microstructure will be described in detail with reference to FIGS. 3 to 5.

The plurality of nanocolumns, which are included in the reflectionless window 120, may be complex nanocolumns composed of a plurality of depths. Specifically, in order to improve the reflectionless effect when the light with various wavelengths is transmitted, a plurality of nanocolumns having a plurality of depths may be included. The detailed structure of the reflectionless window 120 including the complex nanocolumns will be described in detail with reference to FIG. 7.

In the meantime, the reflectionless window 120 may include a pipe for delivering a drug to be injected onto the surface of the skin 10 or the hypoderma. At this time, the tube for delivering the drug may be a tube passing through the inside of the reflectionless window 120. In the meantime, the reflectionless window 120 may be in a plurality of numbers in accordance with the purpose of use.

The detector 130 may detect light and generate a corresponding signal. Specifically, the detector 130 may detect light irradiated from the light source 110 which passes through the reflectionless window 120 by being reflected or scattered from the surface of the skin 10 or the hypoderma, and generate a corresponding signal. At this time, the light detected by the detector 130 may be ultraviolet rays, visible rays, infrared rays, near-infrared rays, fluorescence, Raman, or the like. In the meantime, the detector 130 may be composed of a plurality of detectors in accordance with the purpose of use.

In FIG. 1, it has been described that the light source 110/detector 130 and the reflectionless window 120 are spaced apart from each other, but in actual implementation, the light source 110/detector 130 and the reflectionless window 120 may be in contact. In addition, in FIG. 1, it is shown that the reflectionless window 120 and the skin 10 are spaced from each other, but in actual implementation, the reflectionless window 120 may be implemented in the form of penetrating the skin 10.

Although not illustrated, the sensor 100 may further include a filter (not shown) capable of transmitting only light of a specific wavelength. Specifically, the sensor 100 may include a filter (not shown) in at least one of between the light source 110 and the reflectionless window 120, between the detector 130 and the reflectionless window 120, and between the reflectionless window 120 and the skin 10. At this time, there may be a plurality of filters (not shown), and the filters may transmit different wavelength ranges. Accordingly, the sensor 100 may transmit only the light of a desired wavelength, and irradiate or detect the same.

Figure 2:
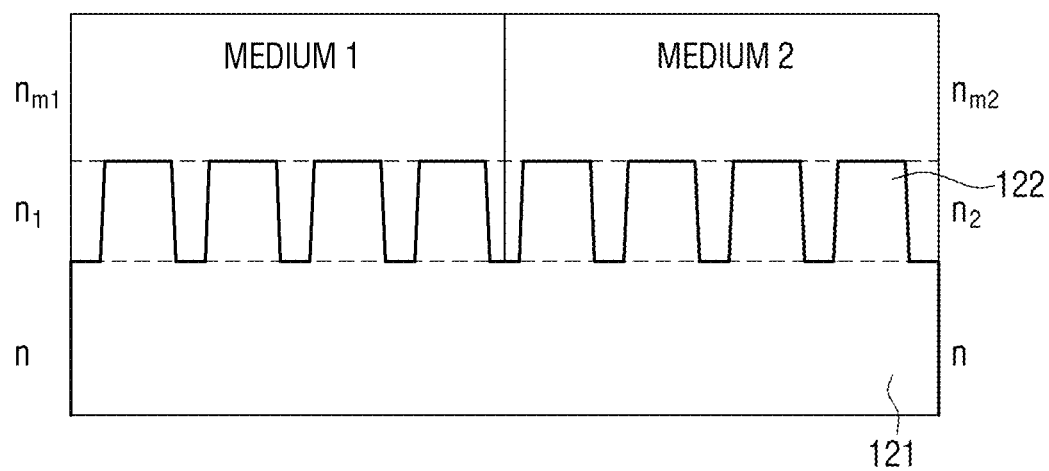
FIG. 2 is a view provided to describe a structure of a reflectionless window according to an embodiment.

FIG. 2 is a view provided to describe a structure of a reflectionless window according to an embodiment.

Referring to FIG. 2, the reflectionless window 120 may include a transparent window 121 and a plurality of nanocolumns 122. Specifically, the reflectionless window 120 may include the transparent window 121 and a plurality of nanocolumns 122 arranged on one surface of the transparent window 121. At this time, the transparent window 121 and the plurality of nanocolumns 122 constituting the reflectionless window 120 may be made of the same material, or the transparent window 121 and the plurality of nanocolumns 122 may be integrally formed.

Specifically, the transparent window 121 may be transparent glass, plastic, or polymer which may pass light, such as one of the glass, acrylic, polyethylene terephthalate (PET), polyethylene naphthalate (PEN), polymethylmethacrylate (PMMA), colorless polyimide (CPI), polyethylene, polypropylene, polysulfone, polyurethane, polyether ether ketone, polythermide, polycarbonate, polyaniline, cyclic olefin copolymer, and silk, and the plurality of nanocolumns 122 may be the same material as the transparent window 121.

At this time, the refractive index of the transparent window 121 constituting the reflectionless window 120 may be n, and the refractive index of the medium 1 in contact with the surface of the reflectionless window 120 may be $n_{m1}$. The medium 1 may be either liquid or gas. The refractive index of the plurality of nanocolumns 122 may be n in the same manner as the transparent window 121 and the refractive index of the medium 1 filled between the plurality of nanocolumns 122 may be $n_{m1}$. However, the plurality of nanocolumns 122 and the medium 1 filled between the plurality of nanocolumns 122 are alternately present, and thus, the effective refractive index of the reflectionless structured layer which includes the plurality of nanocolumns 122 and the medium may be $n_1$ which is between n and $n_{m1}$.

As such, as the reflectionless structured layer of which the refractive index is $n_1$ is formed between the transparent window 121 having the refractive index of n and the medium having the refractive index of $n_{m1}$, when the light travels in a direction of medium 1 from the reflectionless window 120, the light reflected at the boundary of the transparent window 121 and the reflectionless structured layer and the light reflected at the boundary of the reflectionless structured layer and medium 1 is destructively interfered and all the light may be transmitted without being reflected. At this time, when the height of the plurality of nanocolumns 122 is between 100 nm and 150 nm, and a volume of the plurality of nanocolumns 122 and the volume of the medium filled between the plurality of nanocolumns 122 has a ratio of 1:1, the reflectionless effect may be maximized.

In the meantime, according to the refractive index of the medium (medium 1 and medium 2) which is in contact with the surface of the reflectionless window 120, the effective refractive ratio of the reflectionless structured layer including the plurality of nanocolumns 122 and the medium may become different. Specifically, if the refractive index of the reflectionless structured layer formed at the boundary between the reflectionless window 120 and the medium 1 is $n_1$, the refractive index of the reflectionless structured layer formed at the boundary between the reflectionless window 120 and the medium 2 may be formed as $n_2$. This is because the medium filled between the plurality of nanocolumns 122 is medium 2 of which refractive index is $n_{m2}$ which is different from medium 1 of which refractive index is $n_{m1}$.

As described above, the reflectionless structured layer which is varied according to a medium in contact with the reflectionless window 120 and has a refractive index suitable for the environment is formed and thus, the reflectionless window 120 may be used in various media without a separate process, thereby lowering production costs and improving convenience of a user.

In FIG. 2, it has been described that a plurality of nanocolumns 122 are formed in a square shape, but in actual implementation, the plurality of nanocolumns 122 may be in a shape of a cylinder, a cone, a polygonal column, or a polypyramid shape, or an upper surface of the plurality of nanocolumns 122 may be formed in the shape of a curved surface, and the height of each nanocolumn may be varied.

A plurality of nanocolumns having the height shorter than the plurality of nanocolumns 122 may be further included in at least one of the upper surface and the side surface of each of the plurality of nanocolumns 122 or an area where the plurality of nanocolumns 122 are not arranged among a surface of the transparent window 121. The specific structure of the reflectionless window 120 of which the height of the nanocolumn is complex will be described in detail with reference to FIG. 7.

In the meantime, the reflectionless window 120 may further include a microstructure in the form of a needle for penetrating the skin, and various embodiments including the microstructure are described in detail with reference to FIGS. 3 to 5 below.

Figure 3:
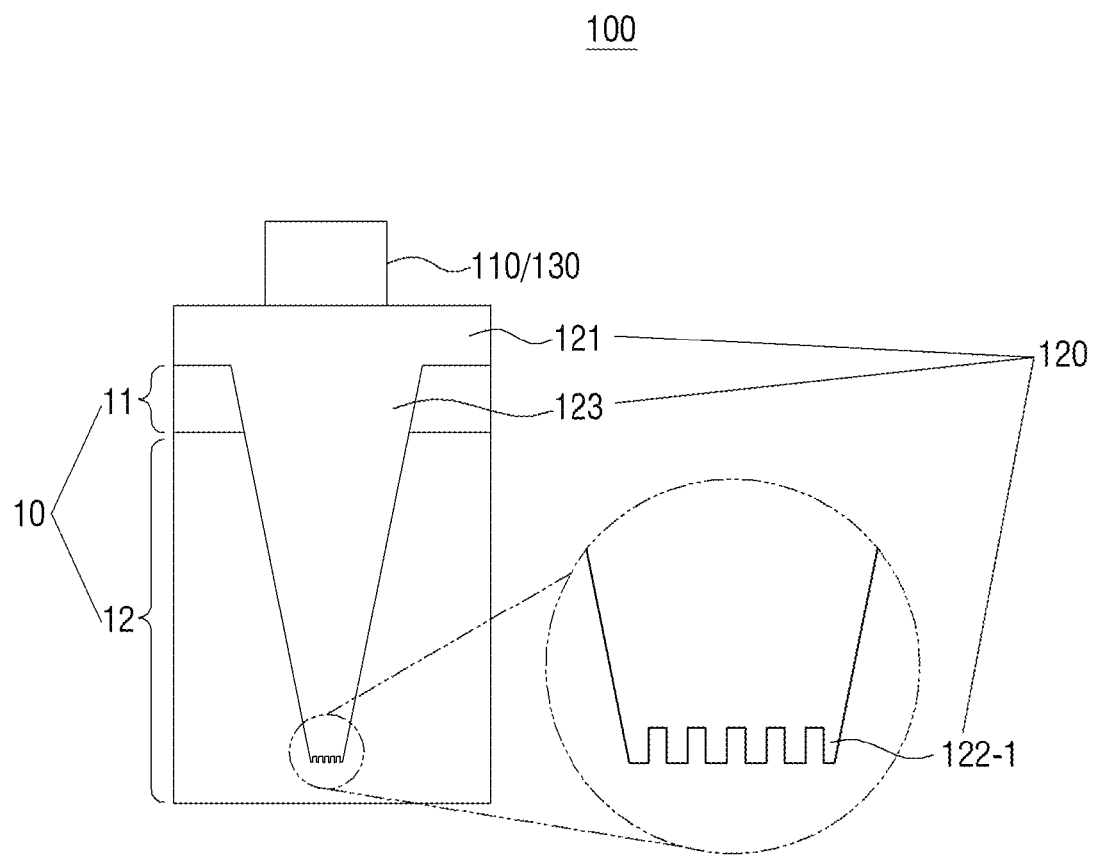
FIGS. 3 to 5 are views briefly illustrating an invasive sensor including a reflectionless window according to various embodiments.
Figure 4:
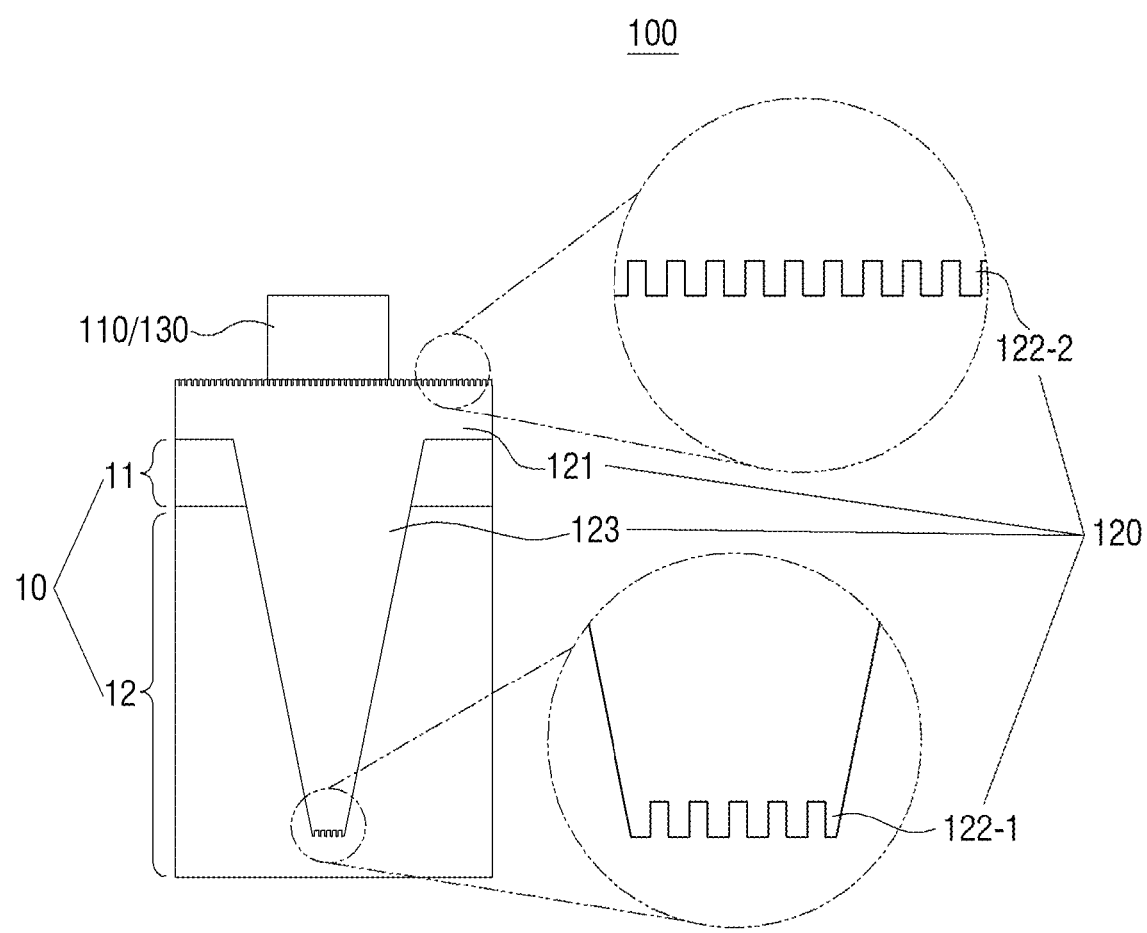
Figure 5:
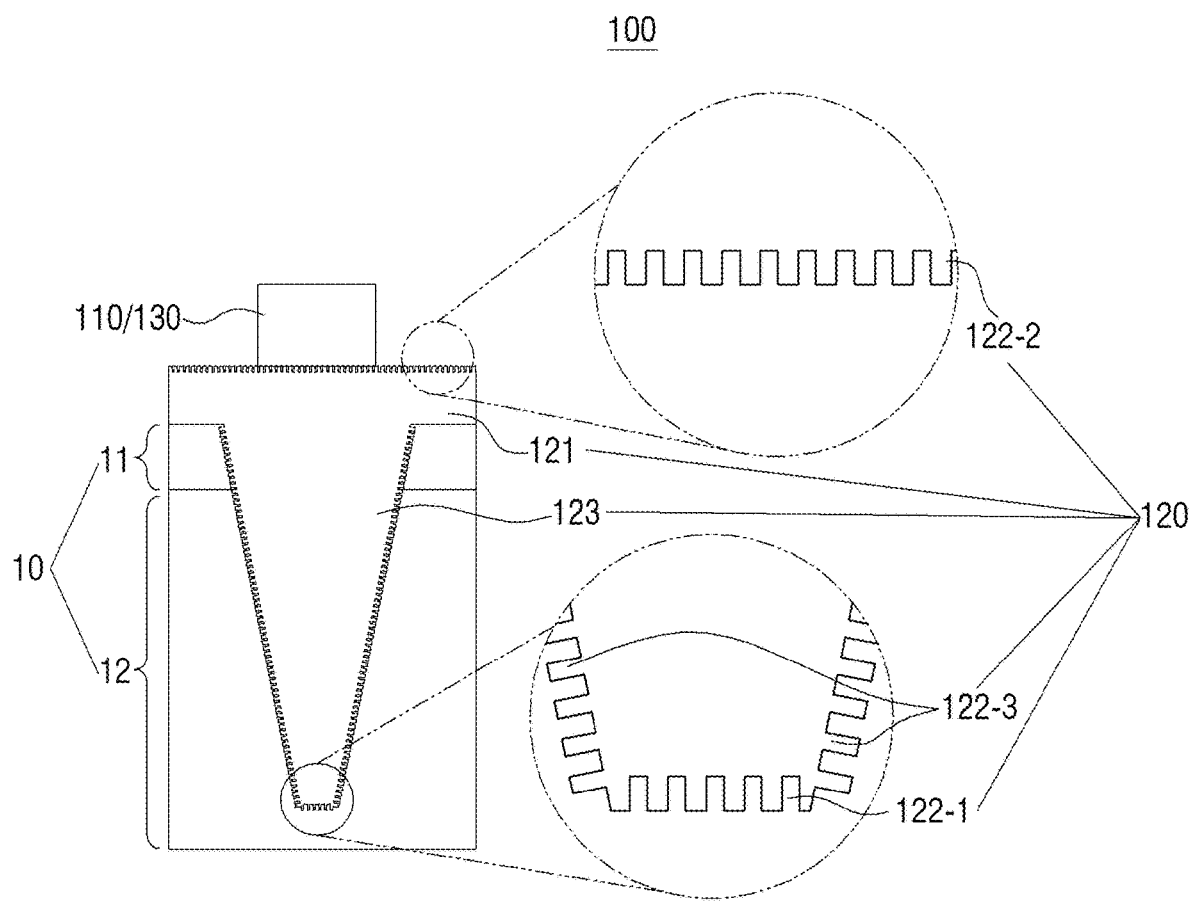

FIGS. 3 to 5 are views briefly illustrating an invasive sensor including a reflectionless window according to various embodiments.

Referring to FIG. 3, the sensor 100 may include the light source 110, the reflectionless window 120, and the detector 130. For convenience of description, it has been described that the light source 110 and the detector 130 are included in one configuration, but in actual implementation, the light source 110 and the detector 130 may be separate configurations. In addition, for convenience of description, only one light source 110 and the detector 130 are described, but a plurality of light sources 110 and a plurality of detectors 130 may be included according to the purpose of the use of the sensor. In the meantime, the characteristics of the light source 110 and the detector 130 are the same as those of FIG. 1 and will not be further described.

At this time, the sensor 100 may be an invasive sensor enabling sensing or treatment of the area the hypoderma. Accordingly, the reflectionless window 120 may include a transparent window 121, a microstructure 123, and a plurality of nanocolumns 122-1.

Specifically, one surface of the transparent window 121 may be in contact with the light source 110/detector 130, and the microstructure 123 may be disposed on the other surface of the transparent window 121. For example, when the microstructure 123 is arranged on the upper part of the transparent window 121, the light source 110/detector 130 may be arranged on a lower part of the transparent window 121.

At this time, the microstructure 123 may be in the form of a needle for penetrating a layer of the skin 10. Specifically, the microstructure 123 may be in the form of at least one of polygonal pyramids or cones including triangular pyramids, quadrangular pyramids, or the like. At this time, the microstructure 123 may penetrate the corneum layer 11 of the surface of the skin 10 and a skin layer 12 below the corneum.

The angle of the side inclination of the microstructure 123 may be various. Specifically, the side inclination may be variously formed according to the purpose of use of the reflectionless window 120. For example, if the purpose is to irradiate light for local sensing or treatment the end of the microstructure 123, that is, the vertex region, a sharp microstructure 123 may be formed by making the side inclination sharp, and if the purpose is to irradiate light for sensing or the treatment of a wide area, a side inclination may become gentle, and a more blunt microstructure 123 may be formed.

In the meantime, FIG. 3 illustrates that one microstructure 123 is included for convenient description, but in actual implementation, a plurality of microstructures 123 may be arranged on the transparent window 121 in an array format.

In the meantime, the microstructure 123 may include a plurality of nanocolumns 122-1 at the ends thereof. Specifically, a plurality of nanocolumns 122-1 may be arranged on a surface of the microstructure 123 opposite to a surface in contact with the transparent window 121 of the microstructure 123. For example, the plurality of nanocolumns 122-1 may be arranged in the apex region of the microstructure 123 in the form of a cone or polypyramid.

In the meantime, the plurality of nanocolumns 122-1 may be a complex nanocolumn having a plurality of heights. This will be described in detail with reference to FIG. 7 below.

As described above, according to the microstructure penetrating the skin of the reflectionless window 120 in the disclosure, the light irradiated from the light source may avoid the corneum which is strongly reflected and absorbed by the light and be directly transmitted to a target region, and depth of the target region may also be adjusted. In addition, the reflectionless window 120 according to the disclosure may minimize the loss caused by the light transmitted from the light source passing through the boundaries of different media, because of the plurality of nanocolumns 122-1.

Referring to FIG. 4, the sensor 110 may include the light source 110, the reflectionless window 120, and the detector 130. For convenience of description, it is described that the light source 110 and the detector 130 are included, but in actual implementation, the light source 110 and the detector 130 may be a separate configuration. In the meantime, the feature of the light source 110 and the detector 130 is the same as the feature described in of FIG. 1, a detailed description thereof is omitted.

At this time, the reflectionless window 120 may include the transparent window 121, the microstructure 120, and the plurality of nanocolumns 122-1 and 122-2.

Specifically, the reflectionless window 120 may further include a plurality of nanocolumns 122-2 on one surface of the transparent window 121 which is in contact with the light source 110 and the detector 130. At this time, on another surface of the transparent window 121, the microstructure 123 may be arranged. For example, when the microstructure 123 is arranged on the upper part of the transparent window 121, the light source 110/detector 130 may be arranged on the lower part of the transparent window 121. In the meantime, it has been described that the light source 110/detector 130 are in contact with the reflectionless window 120, but in actual implementation, the light source 110/detector 130 and the reflectionless window 120 may be spaced apart from each other.

In the meantime, the features of the microstructure 123 included in the reflectionless window 120 and the plurality of nanocolumns 122-1 disposed at an end of the microstructure 123 are the same as the description of FIG. 3, and overlapping description will be omitted.

In the meantime, the plurality of nanocolumns 122-2 formed at one surface of the transparent window 121 which is in contact with the light source 110/detector 130 may be a complex nanocolumn having a plurality of heights. This will be further described with reference to FIG. 7 below.

As described above, the reflectionless window 120 according to the disclosure may avoid the corneum which strongly reflects and absorbs light irradiated from the source of light by the microstructure which passes through the skin, transmit the light directly to a target region, and adjust depth as well. In addition, the reflectionless window 120 according to the disclosure may minimize the loss caused by the light transmitted from the light source through the plurality of nanocolumns 122-1 and 122-2 by passing through the boundaries of different media. Particularly, the loss caused when the light irradiated from the light source enters the reflectionless window may be minimized.

Referring to FIG. 5, the sensor 100 may include the light source 110, the reflectionless window 120, and the detector 130. For convenient description, it has been described that the light source 110 and the detector 130 are included in one configuration, but in actual implementation, the light source 110 and the detector 130 may be separate configurations. In the meantime, the characteristics of the light source 110 and the detector 130 are the same as the description of FIG. 1 and will not be further described.

At this time, the reflectionless window 120 may include the transparent window 121, the microstructure 123, and a plurality of nanocolumns 122-1, 122-2, and 122-3. Specifically, the reflectionless window 120 may further include a plurality of nanocolumns 122-3 on the side surface of the microstructure 123. In the meantime, in FIG. 5, for convenient description, it has been described that a plurality of nanocolumns 122-3 arranged on the side surface of the microstructure 123 are formed in the lateral direction of the microstructure 123, but in actual implementation, the plurality of nanocolumns 122-3 may be formed in the same direction as the plurality of nanocolumns 122-1 arranged at the ends of the microstructure 123.

In the meantime, the features of the microstructure 123 included in the reflectionless window 120, the plurality of nanocolumns 122-1 arranged at the ends of the microstructure 123, and the plurality of nanostructures 122-2 formed at one surface of the transparent window 121 which is in contact with the light source 110/detector 130 are the same as the descriptions in FIG. 3, and FIG. 4, and overlapping descriptions will be omitted.

In the meantime, the plurality of nanocolumns 122-3 formed at a side surface of the microstructure 123 may be complex nanocolumns having a plurality of heights. This will be further described with reference to FIG. 7 below.

As described above, the reflectionless window 120 according to the disclosure may avoid the corneum, which is strongly reflected and absorbed by the light irradiated from the light source by the microstructure penetrating the skin, directly transmit light to a target region, and depth may also be adjusted. In addition, the reflectionless window 120 according to the disclosure may minimize the loss caused by the light transmitted from the light source through the plurality of nanocolumns 122-1, 122-2, and 122-3 passing through the boundaries of different media.

Figure 6:
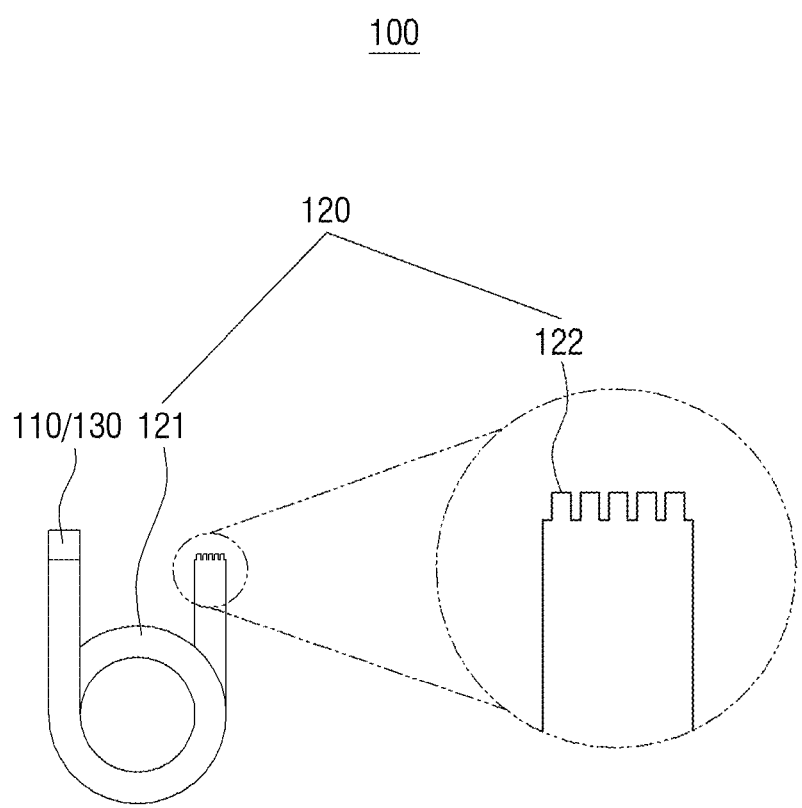
FIG. 6 is a view briefly illustrating a sensor including a reflectionless window in a shape of an optical fiber according to another embodiment.

FIG. 6 is a view briefly illustrating a sensor including a reflectionless window in a shape of an optical fiber according to another embodiment.

Referring to FIG. 6, the sensor 100 may include the light source 110, the reflection window 120, and the detector 130. For convenient description, it has been illustrated that the light source 110 and the detector 130 are included in one configuration, but in actual implementation, the light source 110 and the detector 130 may be separate configurations. In the meantime, the features of the light source 110 and the detector 130 are the same as the description of FIG. 1, and the detailed description will be omitted.

At this time, the sensor 100 may include an optical fiber in the form of a flexible fiber. Accordingly, the reflectionless window 120 may include the transparent window 121 in the form of an optical fiber and a plurality of nanocolumns 122. Here, the optical fiber means an optical fiber in which the glass having a high refractive index is used for the central portion and the glass having a low refractive index is used for the outer portion, so that light passing through the central glass is totally reflected.

Specifically, a plurality of nanocolumns 122 may be arranged on one surface of the transparent window 121 in the form of an optical fiber, and another surface which is opposite to one surface of the transparent window 121 in which the plurality of nanocolumns 122 are arranged may be in contact with the light source 110/detector 130. For example, if a plurality of nanocolumns 122 are arranged at an upper portion of the transparent window 121, the light source 110/detector 130 may be arranged at a lower portion of the transparent window 121. At this time, a plurality of nanocolumns 122 may be in shapes of cylinder, polygonal columns, circular cone, or polypyramid.

Though not illustrated, a plurality of nanocolumns may be arranged on one surface of the transparent window 121 which is in contact with the light source 110/detector 130.

In FIG. 6, it has been illustrated and described that the transparent window 121 and a plurality of nanocolumns 122 are integrally formed, but in actual implementation, it may be implemented such that a panel or film including a plurality of nanocolumns 122 is attached to the ends of the transparent window 121.

Though not illustrated, a microstructure in a shape of a needle may be included in one surface of the transparent window 121 in the form of an optical fiber. At this time, the plurality of nanocolumns 122 may be disposed on at least one of the ends or side surfaces of the needle-shaped microstructure. In the meantime, the microstructure of the needle shape has the same features as the microstructure shown in FIGS. 3 to 5, and a detailed description thereof is omitted.

In the meantime, the plurality of nanocolumns 122 may be complex nanocolumns having a plurality of heights. This will be further described with reference to FIG. 7.

As described above, by the reflectionless window 120 in a flexible optical fiber, accessibility for sensing or treating internal organs to which light may not directly reach, such as esophagus and stomach, may be improved. In addition, the reflectionless window 120 according to the disclosure may minimize loss which occurs while the light transmitted from the light source by the plurality of nanocolumns 122 passes through the boundary of different medium.

Figure 7:
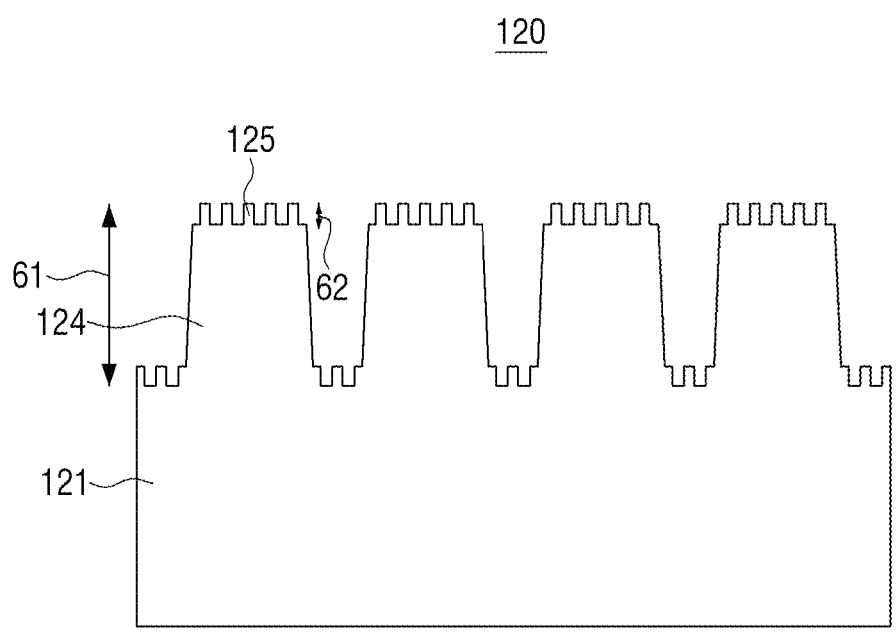
FIG. 7 is a view provided to describe a structure of a reflectionless window according to another embodiment.

FIG. 7 is a view provided to describe a structure of a reflectionless window according to another embodiment.

Referring to FIG. 7, the reflectionless window 120 may include the transparent window 121, a plurality of first nanocolumns 124, and a plurality of second nanocolumns 125. To be specific, the reflectionless window 120 may include the transparent window 121, the plurality of first nanocolumns 124 arranged on a surface of the transparent window 121, and a plurality of second nanocolumns 125 having a height smaller than that of the plurality of first nanocolumns 124, the plurality of second nanocolumns 125 being arranged on the upper surface of the plurality of first nanocolumns 124 and being arranged in an area on a surface of the transparent window 121 in which the plurality of first nanocolumns 124 are not arranged. At this time, the width of the plurality of second nanocolumns 125 may be shorter than the width of the plurality of first nanocolumns 124. In the meantime, in FIG. 7, it has been illustrated and described that the plurality of nanocolumns have two heights, but in actual implementation, the plurality of nanocolumns may have three or more height or width. For example, a plurality of third nanocolumns (not shown) having a width or height shorter than the second nanocolumns 125 may be disposed in the plurality of second nanocolumns 125, and if necessary, a plurality of fourth nanocolumns (not shown) having a width or height shorter than the third nanocolumns may be disposed in the plurality of third nanocolumns. In the meantime, the plurality of second nanocolumns 125 having two or more height or width may be arranged in the plurality of first nanocolumns 124. By this, a reflectionless effect in a wider wavelength range may be expected.

At this time, the plurality of first nanocolumns 124 and the plurality of second nanocolumns 125 may be formed with a material which is the same as the transparent window 121. To be specific, the transparent window 121, a plurality of first nanocolumns 124, and a plurality of second nanocolumns 125 may be formed with any material among polymer series which is transparent or passes light, such as glass, acryl, PET, PEN, PMMA, CPI, polyethylene, polypropylene, polysulfone, polyurethane, polyether ether ketone, polythermide, polycarbonate, polyaniline, cyclic olefin copolymer, silk, or the like.

In the meantime, a plurality of first nanocolumns 124 and a plurality of second nanocolumns 125 may have various shapes. To be specific, the first nanocolumns 124 and the second nanocolumns 125 may have shapes of polygonal columns such as a triangular column and a square column, cylinder, or polypyramid or circular cone of which a space of the upper surface is smaller than a lower surface which is in contact with one surface of the transparent window 121.

In the meantime, in FIG. 7, it has been illustrated and described that a plurality of second nanocolumns 125 are arranged only in each of the upper surface of the plurality of first nanocolumns 124 and in an area where the plurality of first nanocolumns 124 are not arranged among surfaces of the transparent window 121, but in actual implementation, the plurality of second nanocolumns 125 may be arranged at a side surface of the plurality of first nanocolumns 124. As such, as the plurality of second nanocolumns 125 are arranged on at least one of the upper surface or side surface of the first nanocolumns 124, the reflectionless effect for light sources having various incidence angle may be expected.

In the meantime, the first nanocolumns 124 included in the reflectionless window 120 may have a first height 61, and the second nanocolumns 125 may have a second height 62 which is lower than the first height 61. In the meantime, the reflectionless window 120 may have different wavelength ranges in which the reflectionless effect is represented according to the heights of the plurality of nanocolumns of the reflectionless window 120. To be specific, the first height 61 may be between 30 nm and 1000 nm, and the second height 62 may be less than the first height 61. In the meantime, the width of the first nanocolumn 124 may be between 10 nm and 750 nm, and the width of the first nanocolumn 125 may be narrower than the width of the first nanocolumn 124. In the meantime, the numerical figures of the plurality of nanocolumns will be further described with reference to FIG. 8.

As described above, as the reflectionless structure includes complex nanocolumns having a plurality of heights, the reflectionless effect in a wider wavelength range may be expected.

Figure 8:
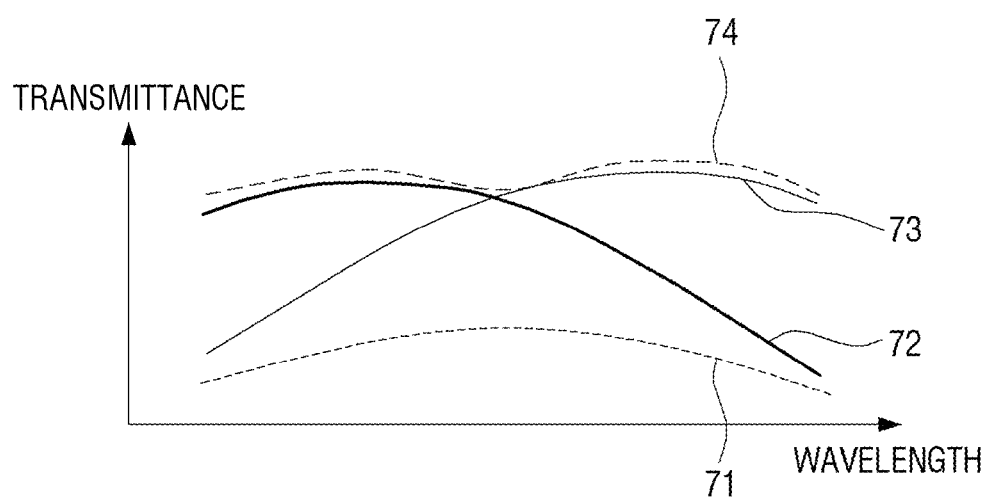
FIG. 8 is a view provided to describe transmittance of a reflectionless window according to wavelength of light which penetrates the reflectionless window according to various embodiments.

FIG. 8 is a view provided to describe transmittance of a reflectionless window according to wavelength of light which penetrates the reflectionless window according to various embodiments.

Referring to FIG. 8, the transmittance according to wavelengths in various embodiments may be identified. To be specific, transmittance of a window 71 without the reflectionless structure, a window 72 including nanocolumns having a height corresponding to an ultraviolet rays area, a window 73 including nanocolumns having a height corresponding to an infrared rays area, and a window 74 including the nanocolumns having a height corresponding to the ultraviolet rays area and nanocolumns having a height corresponding to infrared rays areas may be identified.

To be specific, the window 71 without the reflectionless structure has a low transmittance for overall wavelengths, and the window 72 including nanocolumns having a height corresponding to the ultraviolet rays area has high transmittance in ultraviolet rays area having a short wavelength, but transmittance decreases gradually, as wavelength gets longer.

The window 73 including nanocolumns having a height corresponding to infrared rays has high transmittance in an infrared rays area having long wavelength, but transmittance decreases gradually as the wavelength becomes short. The window 74 which includes both the nanocolumns having a height corresponding to ultraviolet rays area and nanocolumns having a height corresponding to infrared rays have mixed features of the two windows, and it may be identified that transmittance is high for overall wavelength.

The table below represents the optimal condition for reflectionless effect according to a range of wavelength of light.

|  | Wavelength | | |
| --- | --- | --- | --- |
| Size | Ultraviolet rays (300 nm) | Visible rays (600 nm) | Infrared rays (1,800 nm) |
| Width | ~35 nm | ~70 nm | ~210 nm |
| Height | ~65 nm | ~130 nm | ~390 nm |

As described above, when both the nanocolumns having a height corresponding to the ultraviolet rays area and the nanocolumns having a height corresponding to infrared rays are included, the visible rays area which is arranged therebetween may secure high penetration as well.

For example, it may be most desirable that the plurality of first nanocolumns arranged at an upper portion of the transparent window have a height of 130 nm to 390 nm corresponding to the infrared rays wavelength area, and the second nanocolumns, arranged on at least one surfaces among the upper surface and side surface of the plurality of first nanocolumns and arranged in an area on one surface of the transparent window in which the plurality of first nanocolumns are not arranged, have a height of 65 nm or below and a width of 35 nm or below.

However, the height of the first nanocolumn and the second nanocolumn is not limited to the information exemplified above, and may have various heights according to purposes of the sensor. The height may be implemented in a diverse manner. For example, the height of the first nanocolumn is 120 nm which is close to the infrared rays wavelength area, from among 65 nm to 130 nm corresponding to the visible rays wavelength area, and the height of the second nanocolumn may be about 20 nm among 65 nm or below corresponding to the ultraviolet rays wavelength area, or the like.

As described above, a plurality of nanocolumns having a plurality of heights respectively corresponding to a plurality of wavelength areas are included and thus, the reflectionless effect in a wavelength area in a wider range may be expected.

In the meantime, the width may be varied according to the heights of the nanocolumns. For example, it may be most desirable that the plurality of first nanocolumns arranged at an upper portion of the transparent window may have a width of 70 nm to 210 nm corresponding to the infrared rays wavelength area, and the second nanocolumns, which are arranged on at least one surface from the upper surface and a side surface of the plurality of first nanocolumns, and be arranged in an area on a surface of the transparent window in which the plurality of first nanocolumns are not arranged, have a width of 35 nm or below.

However, the width of the first nanocolumn and the second nanocolumns is not limited to the exemplified information, and various widths may be included according to purposes of a sensor.

Figure 9:
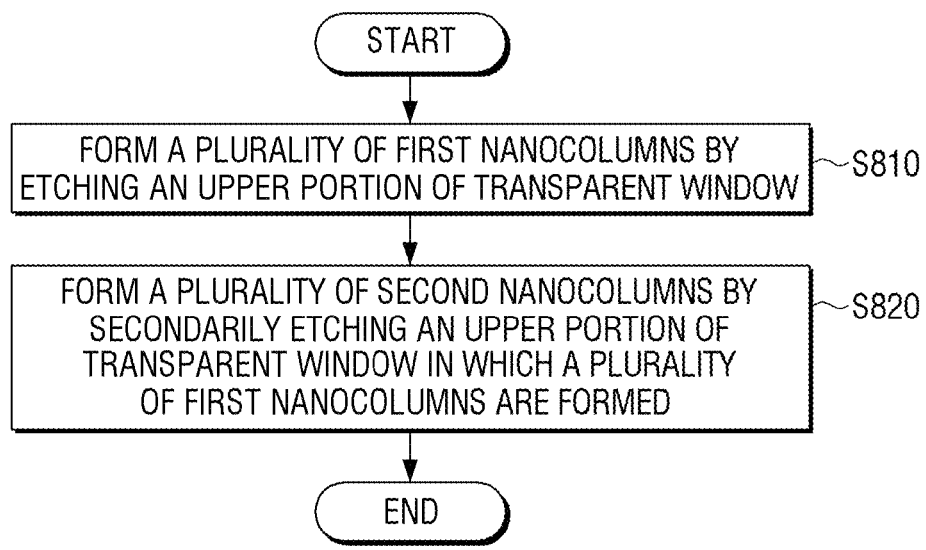
FIGS. 9 to 17 are views provided to describe a method for manufacturing a reflectionless window according to another embodiment.

FIG. 9 is a flowchart to describe a method for manufacturing a reflectionless window according to another embodiment.

Referring to FIG. 9, by etching an upper portion of the transparent window, a plurality of first nanocolumns may be formed in step S810. To be specific, the plurality of first nanocolumns may be formed by arranging a plurality of nanoislands arranged in an upper portion of the transparent window and etching an area where the nanoislands are not arranged. The diameter of the plurality of nanoislands may be 10 nm to 750 nm.

Then, by secondarily etching the upper portion of the transparent window where the plurality of first nanocolumns are formed, a plurality of second nanocolumns may be formed in step S820. To be specific, the plurality of second nanocolumns may be formed by arranging the plurality of nanoislands in an upper portion of the transparent window in which the plurality of first nanocolumns are formed and etching an area where the nanoislands are not arranged. At this time, the diameter of the plurality of nanoislands which are arranged to form the plurality of second nanocolumns may be smaller than the diameter of the plurality of nanoislands arranged to form the plurality of first nanocolumns. In the meantime, the plurality of second nanocolumns may be arranged on at least one surface among the upper surface of the plurality of first nanocolumns and side surface thereof, and be arranged in an area on a surface of the transparent window in which the plurality of first nanocolumns are not arranged.

It has been described that etching is performed to form a plurality of nanocolumns, but in actual implementation, nanocolumns may be formed by a patterning technology of fabricating and stamping out a mold or a stamp according to a pattern of a plurality of nanocolumns.

Specifically, a transparent window may be formed by fabricating a mold by removing a mold substrate according to patterns of a plurality of nanocolumns, filling up and solidifying the removed space with liquid glass, liquid polymer, or the like and then removing the mold.

At this time, the mold substrate may use hard material such as silicone and glass, and a flexible material such as poly(dimethylsiloxane) (PDMS), or the like. The mold may be fabricated by etching the mold substrate according to the patterns of the plurality of nanocolumns.

As such, when the transparent window including a plurality of nanocolumns is formed using a mold or a stamp, a plurality of transparent windows having the same structure may be produced using one mold or stamp and thus, it is expected that the mass production capability would be improved.

In the meantime, in the above process, the step of removing nanoislands after etching according to types of the arranged nanoislands may be further included. To be specific, when the nanoislands are removed together in an etching stage, it is not necessary to further include a step of removing the nanoislands after etching. This will be further described with reference to FIGS. 10 to 13.

In the meantime, when the nanoislands are not removed together in the etching stage, the step of removing the nanoislands after etching may be further included. This will be described in greater detail with reference to FIGS. 14 to 16.

FIGS. 10 to 13 are views provided to describe a method for manufacturing a reflectionless window according to an embodiment in which nanoislands are etched together in the stage of etching for forming nanocolumns.

Figure 10:
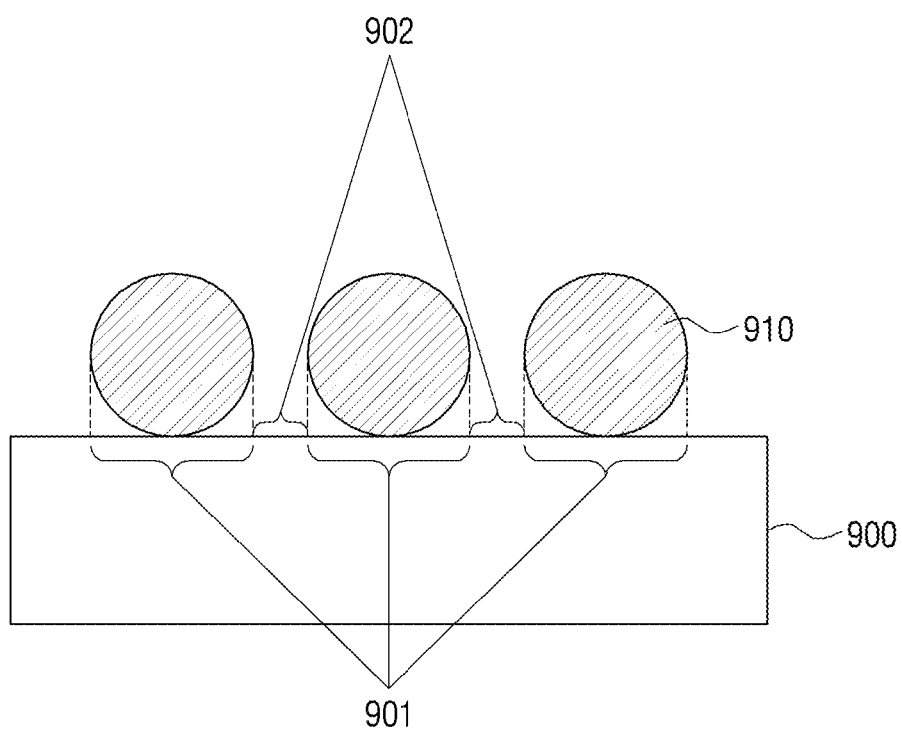

Referring to FIG. 10, a plurality of nanoislands 910 may be arranged on an area 901 where the plurality of first nanocolumns will be formed at an upper portion of a transparent window 900 which is a parent material. At this time, the plurality of first nanoislands 910 may be nano particles, nano spheres, or the like. While an area 902 in which the plurality of first nanocolumns are not formed is being etched, the first nanoislands 910 may be etched together and removed. To be specific, the plurality of first nanoislands 910 may be polystyrene, glass, or the like.

Figure 11:
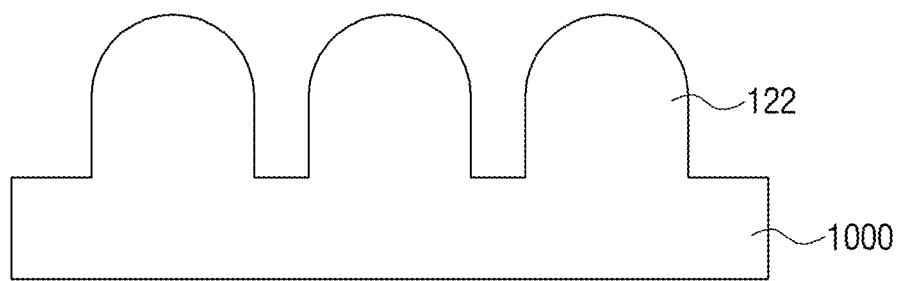

When etching is completed, as illustrated in FIG. 11, a transparent window 1000 in which the plurality of first nanocolumns 122 are arranged may be formed. Specifically, in the process of etching the area 902 in which the plurality of first nanocolumns are not formed, the plurality of first nanoislands 910 arranged at the area 901 in which the plurality of first nanocolumns will be formed are etched together, but the area 901 in which the plurality of first nanoislands are to be formed may not be etched, and when the etching is completed, an area where the first nanoislands 910 are arranged may remain as a shape of a column. In addition, the plurality of the first nanoislands 910 are removed in the process of etching, and the step of removing the plurality of first nanoislands 910 may not be separately required. In the meantime, even though the plurality of the first nanoislands 910 are etched together, if the plurality of nanoislands 910 are not completely removed, the step of removing the remaining nanoislands may be separately included.

Figure 12:
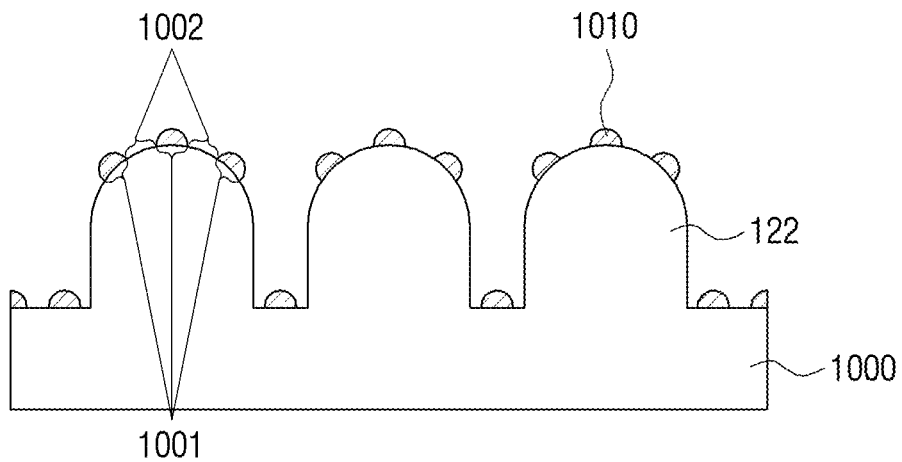

Then, as illustrated in FIG. 12, a plurality of second nanoislands 1010 may be arranged on an upper portion of the transparent window 1000 in which the plurality of first nanocolumns 122 are formed. Specifically, the second nanoislands 1010 which are smaller than the first nanoisland may be arranged on the area 1001 in which the plurality of second nanocolumns will be formed on the upper portion of the plurality of first nanocolumns 122 and an area in which the first nanocolumns 122 are not arranged from among an upper portion of the transparent window. In the meantime, FIG. 12 illustrates that the second nanoislands 1010 are arranged on an upper portion of the first nanoislands 122, but in actual implementation, the second nanoislands 1010 may be arranged on the upper surface and side surface of the first nanocolumn 122, or only on the side surface of the first nanoisland 122.

At this time, the plurality of second nanoislands 1010 may be nano particles, nano spheres, or the like, and as the area 1002 where the plurality of second nanocolumns are not formed is etched, the second nanoislands 1010 may be etched together and removed. Specifically, the plurality of second nanoislands 1010 may be polystyrene, glass, or the like.

Figure 13:
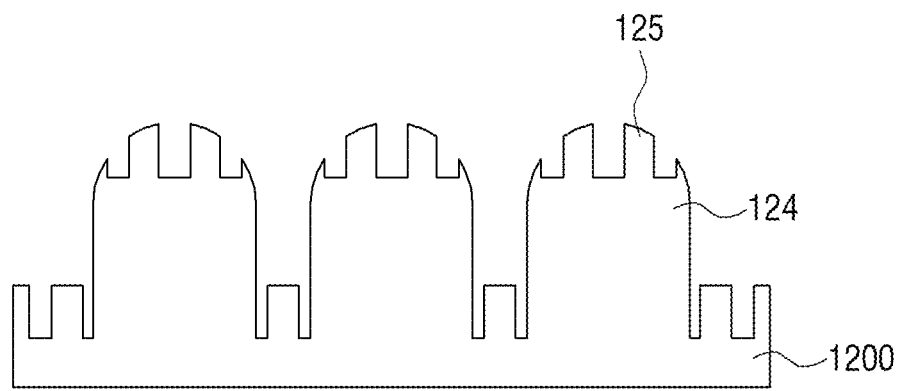

When the secondary etching is completed, as illustrated in FIG. 13, a transparent window 1200 in which the plurality of first nanocolumns 124 and the plurality of second nanocolumns 125 are arranged on an upper surface of the plurality of first nanocolumns 124 and an area in which the plurality of first nanocolumns 124 are not arranged may be formed. To be specific, in the process of secondary etching of the area 1002 in which the plurality of second nanocolumns are not formed, the plurality of second nanoislands 1010 which are arranged on the area 1001 in which the plurality of second nanocolumns are to be formed are etched together, but the area 1001 in which the plurality of second nanocolumns are to be formed are not etched. Accordingly, when the etching is completed, the area in which the second nanoislands 1010 are arranged may remain in the shape of the column. In addition, the plurality of second nanoislands 1010 are removed in the process of etching and thus, the step of removing the plurality of second nanoisland 1010 may not be separately required. In the meantime, even though the plurality of second nanoislands 1010 are etched together, if the plurality of second nanoislands 1010 are not completely removed, the step of removing remaining nanoislands may be separately included.

In FIG. 13, it has been illustrated for convenience description that the plurality of second nanocolumns 125 are formed only in an upper surface of the plurality of first nanocolumns 124, but in actual implementation, if necessary, the plurality of second nanocolumns 125 may be formed at an upper surface or side surface of the plurality of first nanocolumns 124 or only at the side surface of the plurality of the first nanocolumns 124.

FIGS. 14 to 17 are views provided to describe a method for manufacturing a reflectionless window according to another embodiment.

Figure 14:
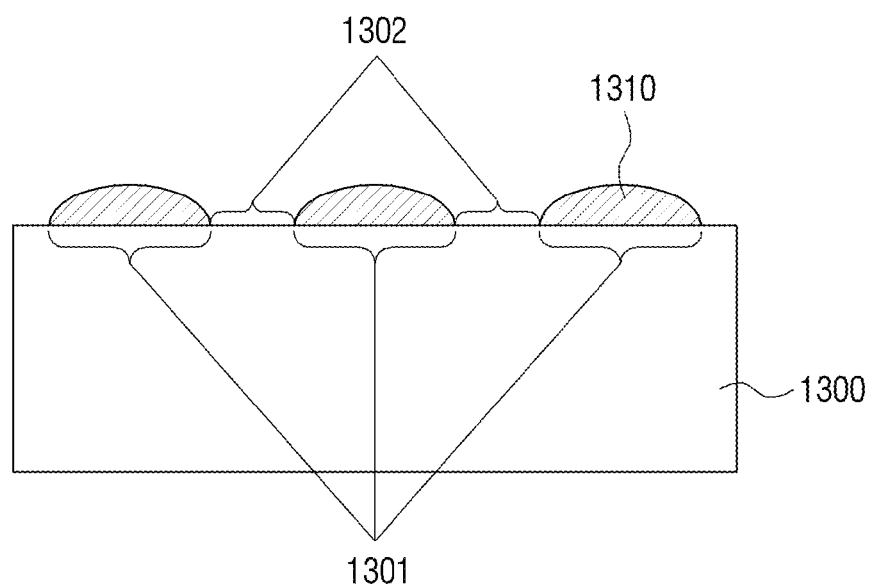
Figure 15:
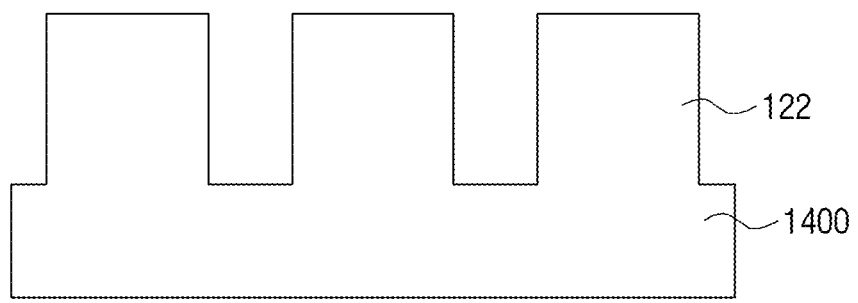

Referring to FIG. 14, first of all, a plurality of first nanoislands 1310 may be formed in an area 1301 in which the plurality of the first nanocolumns will be formed at an upper portion of the transparent window 1300 which is the parent material. At this time, the plurality of first nanoislands 1310 may be a patterned mask shape, or may not be removed in the process of etching the area 1002 in which the plurality of first nanocolumns are not formed. At this time, the plurality of first nanoislands 1310 may be at least one of metal and photoresist. To be specific, metal may be gold, silver, aluminum, chrome, copper, titanium, or the like, and the photoresist may be a material which is used for a photoresist mask such as AZ series, SU-8, or the like.

When etching is completed, as illustrated in FIG. 11, a transparent window 1400 in which the plurality of first nanocolumns 122 are arranged may be formed. To be specific, in the process of etching the area 1302 where the plurality of first nanocolumns are not formed, the area 1301 in which the plurality of first nanocolumns are to be formed is not etched by the arranged plurality of first nanoislands 1310, and when etching is completed, the area in which the first nanoislands 1310 are arranged may remain in a shape of a column. In addition, after the etching is completed, the step of removing the first nanoisland 1310 may be further included.

Figure 16:
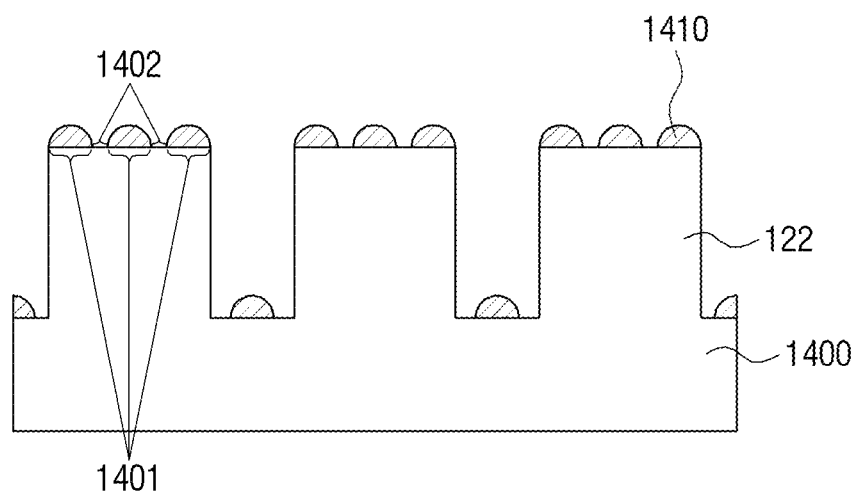

Then, as illustrated in FIG. 16, a plurality of second nanoislands 1410 may be arranged on an upper portion of a transparent window 1400 in which the plurality of first nanocolumns 122 are formed. To be specific, second nanoislands 1410 which are smaller than the first nanoislands may be arranged on an area 1401 in which the plurality of second nanocolumns are to be formed on the upper surface of the plurality of first nanocolumns 122 and an area in which the plurality of first nanocolumns 122 are not arranged from among an upper area of the transparent window. In the meantime, FIG. 16 illustrates and describes that the second nanoislands 1410 are arranged only on an upper area of the first nanocolumns 122, but in actual implementation, the second nanoislands 1410 may be arranged on an upper surface and a side surface of the first nanocolumns 122, or only in a side surface of the first nanocolumns 122, if necessary.

At this time, the plurality of second nanoislands 1410 may be a patterned mask shape, or may not be removed in the process of secondary etching of the area 1402 in which the plurality of second nanocolumns are not formed, and a separate removing step may be required. To be specific, the plurality of second nanoislands 1410 may be at least one of metal and photoresist. To be specific, the metal may be gold, silver, aluminum, chrome, copper, titanium, or the like, and the photoresist mask may be a material which is used for a photoresist mask such as AZ series, SU-8, or the like.

Figure 17:
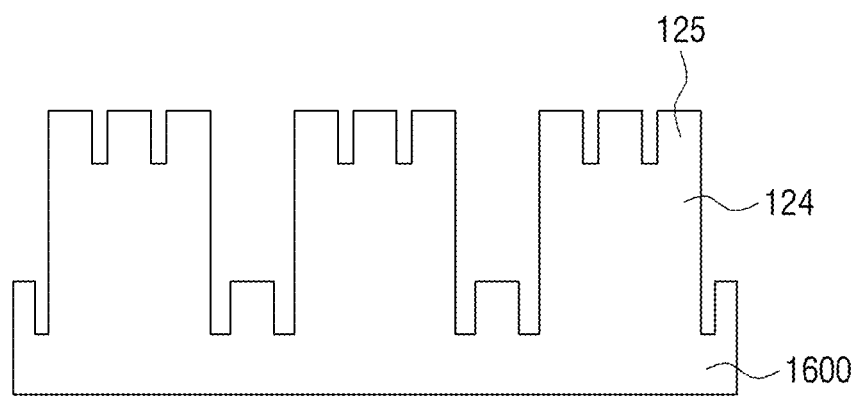

When the secondary etching is completed, as illustrated in FIG. 17, a transparent window 1600 in which the plurality of first nanocolumns 124 and the plurality of second nanocolumns 125 are arranged on an upper surface of the plurality of first nanocolumns 124 and an area in which the plurality of first nanocolumns 124 are not arranged may be formed. To be specific, in the process of etching of the area 1402 in which the plurality of second nanocolumns are not formed, by the plurality of second nanoislands 1410 arranged on the area 1401 in which the plurality of second nanocolumns are to be formed, the area 1401 in which the plurality of nanocolumns are to be formed is not etched, and after etching is completed, the area in which the second nanoislands 1410 are arranged may remain in a shape of a column. In addition, the plurality of second nanoislands 1410 may be present in an upper surface of the second nanocolumns 125 even after the etching, and a separate step of removing the plurality of second nanoislands 1410 may be required. In the meantime, in FIG. 17, it has been described that the plurality of second nanocolumns 125 are formed only at an upper portion of the plurality of first nanocolumns 124 for convenient description, but in actual implementation, a plurality of second nanocolumns 125 may be formed on an upper surface and a side surface of the plurality of first nanocolumns 124 or only on a side surface of the first nanocolumns 124 if necessary.

An embodiment is divided into a case in which the first nanoisland and the second nanoisland are etched in the process of generating a nanocolumn or a case in which the first nanoisland and the second nanoisland are not etched. However, in actual implementation, methods used in two embodiments may be used in a mixed manner. For example, it may be implemented that a nano particle or a nano sphere which may be etched is used as the first nanoisland, and a patterning mask which is not etched is used as the second nanoisland, or vice versa.

Figure 18:
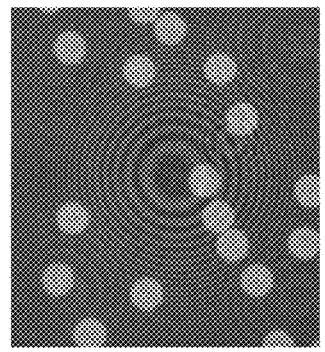
FIG. 18 is a view illustrating an example of an image sensed through a reflectionless window according to an embodiment.
Figure 18:
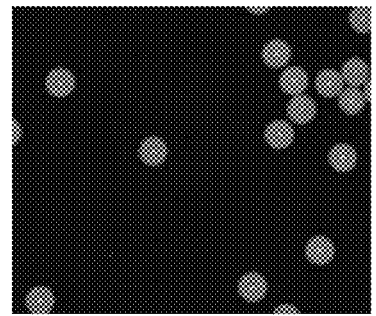

FIG. 18 is a view illustrating an example of an image sensed through a reflectionless window according to an embodiment.

Referring to FIG. 18B, an image generated through sensing using the reflectionless window according to an embodiment is clearer than an image generated through sensing using a window not having a reflectionless structure as illustrated in FIG. 18A. To be specific, the image generated through sensing using the reflectionless window having an excellent transmittance has high contrast as illustrated in FIG. 18B and thus, an object to be observed from an image such as lesion, cancel cells, or the like may be identified more clearly.

Figure 19:
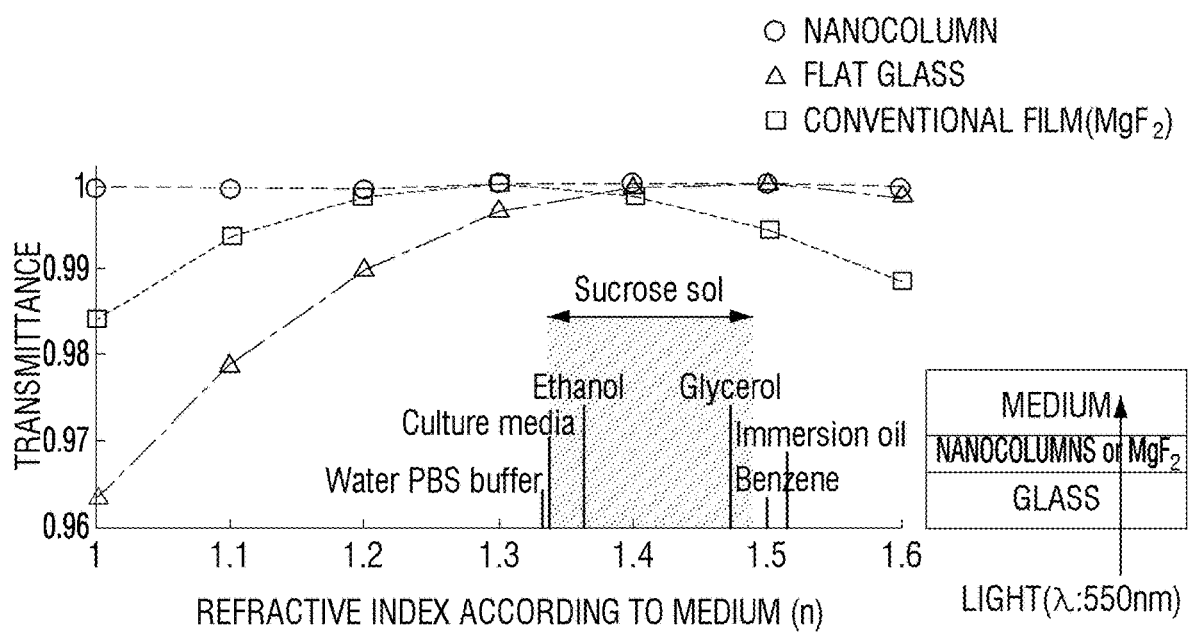
FIG. 19 is a view provided to describe transmittance of a reflectionless window according to a refractive index of a medium which is in contact with a reflectionless window according to an embodiment.

FIG. 19 is a view provided to describe transmittance of a reflectionless window according to a refractive index of a medium which is in contact with a reflectionless window according to an embodiment.

Referring to FIG. 19, when light having a wavelength of 550 nm travels from a glass to a medium having a different refractive index, the transmittance according to the refractive index of the medium may be confirmed. Specifically, when the "nanocolumn" according to an embodiment is included between the glass and the medium, the transmittance appears to be close to 1 regardless of the refractive index of the medium, and thus, it is identified that almost all the light is transmitted.

On the contrary, in the case of the "flat glass", that is, when a separate reflectionless structure is not provided, it is identified that the transmittance decreases sharply as the refractive index of the medium is lowered.

In the case where the conventional film ($MgF_2$), which is a conventional reflectionless film, is included between the glass and the medium, if the refractive index of the medium is lowered, decrease in transmittance is less than that of "flat glass", but if the refractive index of the medium becomes greater than a specific refractive index (about 1.3), it may be confirmed that the transmittance is further reduced as compared with the case where there is no separate reflectionless structure.

As described above, the reflectionless window according to an embodiment may provide an optimal condition of the reflectionlessness regardless of a type of the medium.

Particularly, when a plurality of nanocolumns having a plurality of heights are included, high transmittance may be realized without limitation of transmitted wavelength, and thus, the reflectionless window may be utilized in various fields such as a sensor, display, or the like. cm What is claimed is:

What is claimed is:
1. A reflectionless window comprising:
a transparent window;
a plurality of first nanocolumns arranged on a first surface of the transparent window and a second surface of transparent window which is contacted with a light source; and a plurality of second nanocolumns having a height and a width smaller than a height and a width of the first nanocolumns, the plurality of second nanocolumns being arranged directly on an upper surface and a side surface of the plurality of first nanocolumns and being arranged in an area on a surface of the transparent window in which the plurality of first nanocolumns are not arranged, wherein the height and the width of the first nanocolumns corresponds to a first wavelength of light and the height and the width of the second nanocolumns corresponds to a second wavelength of light, wherein the first surface of the transparent window is disposed in opposite direction of the second surface of the transparent window, wherein the second wavelength is shorter than the first wavelength, and wherein the plurality of second nanocolumns arranged on the side surface protrude in a direction lateral to the side surface.

2. The reflectionless window of claim 1, wherein the plurality of first nanocolumns and the plurality of second nanocolumns are made of a same material as the transparent window.

3. The reflectionless window of claim 1, wherein the first nanocolumn has a height of 130 nm to 390 nm and a width of 70 nm to 210 nm, and wherein the second nanocolumn has a height less than or equal to 65 nm and a width less than or equal to 35 nm.

4. The reflectionless window of claim 1, wherein the transparent window is formed with any one material among glass, acryl, Polyethylene Terephthalate (PET), Polyethylene Naphthalate (PEN), Polymethylmethacrylate (PMMA), Colorless Polyimide (CIP), polyethylene, polypropylene, polysulfone, polyurethane, polyether ether ketone, polythermide, polycarbonate, polyaniline, cyclic olefin copolymer, and silk.

5. The reflectionless window of claim 1, wherein the plurality of first nanocolumns are configured such that a size of an upper surface of the first nanocolumns is smaller than a size of a lower surface of the first nanocolumns, where the lower surface of the first nanocolumns is in contact with a surface of the transparent window.

6. A reflectionless window for a sensor, comprising:
an optical fiber comprising a first end surface and a second end surface;
a transparent window provided on the first end surface of the optical fiber;
a plurality of first nanocolumns arranged on a surface of the transparent window and another surface which is opposite to the surface of the transparent window;
a plurality of second nanocolumns having a height and a width smaller than a height and a width of the first nanocolumns, the plurality of second nanocolumns being arranged directly on an upper surface and a side surface of the plurality of first nanocolumns and being arranged in an area on a surface of the transparent window in which the plurality of first nanocolumns are not arranged, and a light source and a detector provided on the second end surface of the optical fiber, wherein the height and the width of the first nanocolumns corresponds to a first wavelength of light and the height and the width of the second nanocolumns corresponds to a second wavelength of light, wherein the second wavelength is shorter than the first wavelength, and wherein the plurality of second nanocolumns arranged on the side surface protrude in a direction lateral to the side surface.

7. A reflectionless window for an invasive sensor, comprising:
a transparent window;
a microstructure which is arranged on an upper part of the transparent window and has a shape of a needle to penetrate a skin layer;
a plurality of first nanocolumns arranged on an end of the microstructure and lower part of the transparent window which is contacted with a light source; and
a plurality of second nanocolumns having a height and a width smaller than a height and a width of the first nanocolumns, the plurality of second nanocolumns being arranged directly on an upper surface and a side surface of the first nanocolumn and an area where the first nanocolumns are not arranged among ends of the microstructure, wherein the height and the width of the first nanocolumns corresponds to a first wavelength of light and the height and the width of the second nanocolumns corresponds to a second wavelength of light, wherein the second wavelength is shorter than the first wavelength, and wherein the plurality of second nanocolumns arranged on the side surface protrude in a direction lateral to the side surface.

8. The reflectionless window for an invasive sensor of claim 7, further comprising:
a plurality of nanocolumns on a side surface of the microstructure.

9. The reflectionless window for an invasive sensor of claim 7,
wherein the first nanocolumn has a height of 130 nm to 390 nm and a width of 70 nm to 210 nm, and
wherein the second nanocolumn has a height less than or equal to 65 nm and a width less than or equal to 35 nm.

10. The reflectionless window for a sensor of claim 6,
wherein the first nanocolumn has a height of 130 nm to 390 nm and a width of 70 nm to 210 nm, and
wherein the second nanocolumn has a height less than or equal to 65 nm and a width less than or equal to 35 nm.

11. The reflectionless window for a sensor of claim 6,
wherein the transparent window comprises a microstructure in a shape of a needle arranged on an upper part of the transparent window, and
wherein the plurality of first nanocolumns are arranged on at least one of an end or a side surface of the microstructure.

* * * * *